United States Patent [19]

Wonn et al.

[11] B 3,991,603

[45] Nov. 16, 1976

[54] MOISTURE INDICATING APPARATUS

[75] Inventors: James W. Wonn, Irwin; Ronald L. Bannister, Glen Mills, both of Pa.

[73] Assignee: Westinghouse Electric Corporation, Pittsburgh, Pa.

[22] Filed: Mar. 10, 1975

[21] Appl. No.: 557,153

[44] Published under the second Trial Voluntary Protest Program on February 3, 1976 as document No. B 557,153.

[52] U.S. Cl. .................................... 73/29; 60/657; 60/660
[51] Int. Cl.² .................................... G01N 29/02
[58] Field of Search .............. 73/29, 24, 23, 73, 69, 73/70, 194 A, 194 B; 340/239, 261; 60/646, 657, 660; 415/13

[56] References Cited
UNITED STATES PATENTS

| | | | |
|---|---|---|---|
| 3,097,488 | 7/1963 | Eggenberger et al. | 60/660 |
| 3,580,092 | 5/1971 | Scarpa | 73/194 B |
| 3,816,773 | 6/1974 | Baldwin | 73/194 B |
| 3,845,660 | 11/1974 | McDonnell | 73/194 A |
| 3,882,680 | 5/1975 | Durrant et al. | 60/646 |

*Primary Examiner*—Richard C. Queisser
*Assistant Examiner*—Stephen A. Kreitman
*Attorney, Agent, or Firm*—G. H. Telfer

[57] ABSTRACT

A moisture indicating apparatus for indicating the presence of moisture in a vapor flow confined within a conduit. Sonic energy generated within the conduit is detected at predetermined locations along the conduit by non-intrusively mounted detection devices. The sonic energy is converted into an electrical signal and the magnitude of the electrical signal from each detection device and the time difference therebetween are compared to predetermined magnitude and time-difference standards. If the electrical signals indicate the presence of moisture, responsive action is initiated by a suitable control arrangement connected to the apparatus. In addition to indicating moisture presence, the quality of moisture with the vapor flow is detectable.

4 Claims, 2 Drawing Figures

MOISTURE INDICATING APPARATUS

BACKGROUND OF THE INVENTION

1. Field of the Invention

This invention relates to a steam turbine power generation system, and in particular, to an apparatus associated therewith to indicate moisture presence within the steam flow.

2. Description of the Prior Art

The incidence of turbine damage due to the induction of water into the turbine element is an increasing phenomenon in power generation industry. When water enters the turbine serious damage often can occur, often requiring extended periods of turbine inactivity in order to make necessary repairs. The magnitude of the problem has been recognized and appreciated by those in the power generation industry, and has led to the formation of a Turbine Water Damage Prevention Committee Standards Department of the American Society of Mechanical Engineers.

The identification of the causal factors leading to the increase in turbine water damage is difficult. However, whatever the reasons responsible for the creation of water in the vapor flow, one important preventative measure recommended by the Prevention Committee, and embodied in the Standards issued thereby, is the use of apparatus which is able to detect the presence of water droplets in the vapor flow in order to avoid the damage to turbine occasioned thereby.

In the prior art, thermocouple devices are disposed within the turbine cylinder, in the inlet piping, and in other conduit lines leading to the apparatus. However, for the cylinder thermocouple, it is the unfortunate case that the indication of water droplets occurs at a time when damage to the turbine is unavoidable. Similarly, the use of thermocouples in the inlet and extraction lines or other piping leading into the turbine to detect the presence of water therein by the detection of the metal temperature is also of limited value. This is so since, once the metal temperature of the conduit has been lowered sufficiently to substantiate that water droplets or cool vapor is carried within the vapor flow, there is little action that can be taken in time to prevent turbine damage. Also, the disposition of thermocouples within the turbine piping is disadvantageous from a mechanical standpoint. The thermocouples are usually mounted in an intrusive manner, that is, into the body of the piping itself. This leads to local mechanical weakness and is, for this reason, undesirable.

It is apparent that a detection system to detect the presence of moisture droplets within a steam vapor flow within the conduit leading to the turbine so as to prevent water damage thereto is desirable. Such a system must be able to quickly ascertain the presence of the liquid droplets and relay this data to the turbine control system in sufficient time to effectively prevent water damage. The system must be reliable and accurate so that "false alarm" rate is low enough to insure that repeated false shutdowns of the turbine are avoided. Further, the apparatus must preferably obtain the necessary information without intrusive mounting into the conduit so as to avoid mechanical damage thereto. Also, indications as to the quality of the steam conducted within the conduit would be an advantageous and desirable capability for such apparatus.

SUMMARY OF THE INVENTION

The apparatus embodying the teachings of this invention provides an accurate and reliable indication of the presence of moisture in a vapor flow in a steam turbine power generation system. The apparatus for indicating the presence of moisture in a vapor flow confined within a conduit comprises sonic detection means for detecting sonic energy generated by the moisture within the conduit, the sonic detection means being mounted on the conduit in a non-intrusive manner, means for converting the detected sonic energy into an electrical signal, means for comparing the magnitude of the electrical signal and for generating an alarm signal indicative of a difference existing therebetween, and signal means responsive to the alarm signal for indicating to an external observer or for initiating other suitable action that water droplets are present in the vapor flow. The detected signal may be greater or less than a predetermined threshold, depending upon the location of the detector relative to the moisture source. In one embodiment of the invention, detection is obtained at two places on the conduit and the time difference between the sonic signals detected is compared to a predetermined time standard to provide a more reliable indication of the relative quantity of gross moisture present within the vapor flow. In addition, the apparatus is also able to act as a monitor for indicating the quality of the moisture carried within the steam vapor flow.

It is an object of this invention to provide a high sensitivity, fast-responding indicator apparatus for indicating the presence of moisture in a vapor flow confined within a conduit in a steam turbine power generation plant. It is a further object to provide an indication apparatus that provides a nearly zero false alarm rate so as to prevent repeated, non-essential, interruptions in the operation of the steam power plant. It is a further object of this invention to provide an indication apparatus for indicating both the presence and the quality of moisture carried within the vapor flow. It is a still further object to provide apparatus detecting both the presence and quality of moisture and mounted in a non-intrusive manner on the vapor-carrying conduit. Other objects of the invention will become apparent in the detailed description of the preferred embodiment which follows herein.

BRIEF DESCRIPTION OF THE DRAWINGS

The invention will be more fully understood from the following detailed description of a preferred embodiment, taken in connection with the accompanying drawings, in which.

DESCRIPTION OF THE PREFERRED EMBODIMENT

Figure 1:
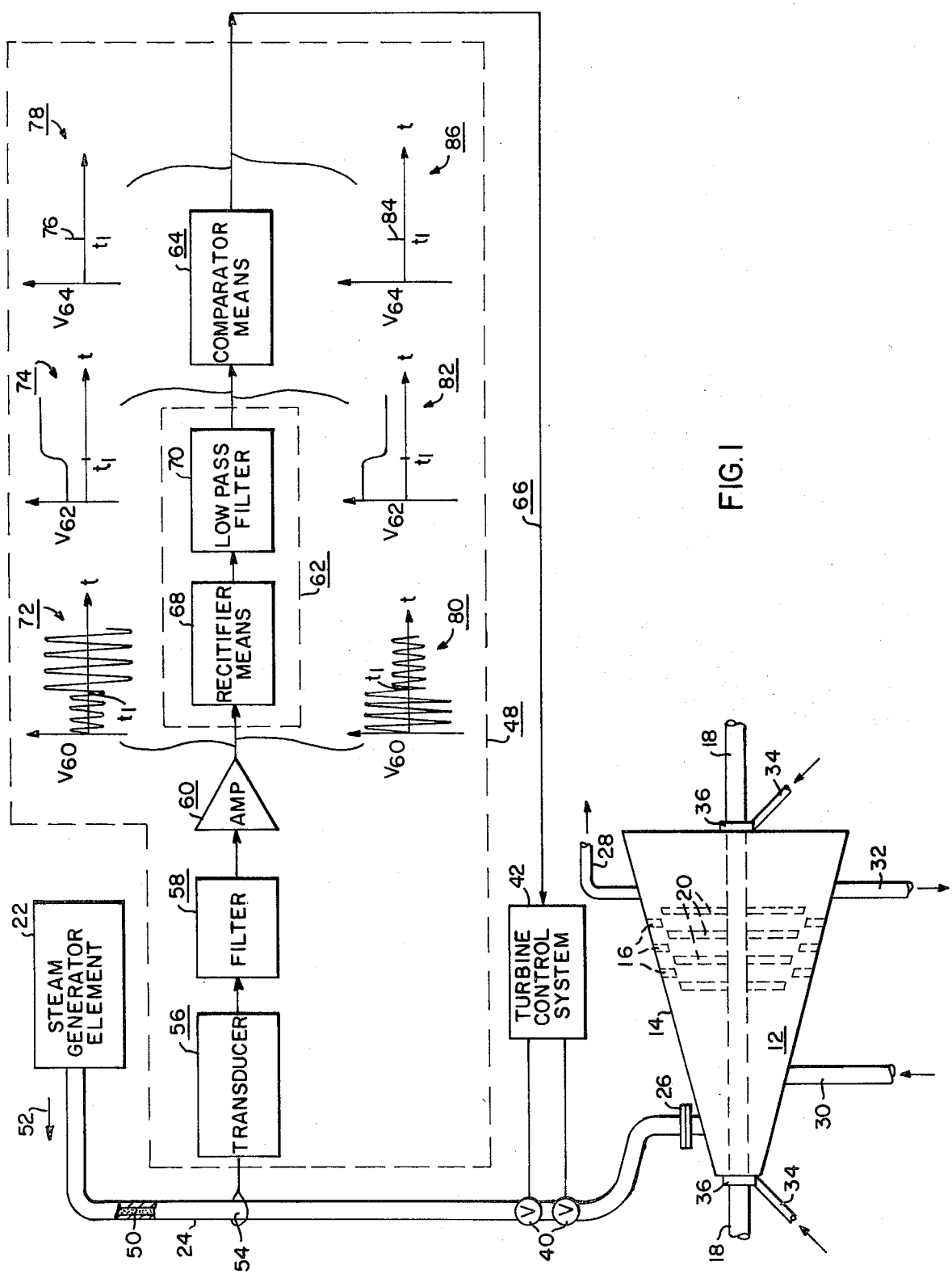
FIG. 1 is a diagrammatic view of a portion of a steam turbine power generation facility having an apparatus for indicating the presence of moisture in a vapor flow conducted within a conduit leading to a steam turbine.

Throughout the following description, similar reference numerals refer to similar elements in all figures of the drawings.

In FIG. 1, a diagrammatic view of a portion of a steam turbine power plant generally indicated by reference numeral 10 is shown. The power plant 10 comprises a turbine element 12 having a casing 14 supporting therein a predetermined number of annular arrays of stationary blades 16. Extending centrally and axially through the casing 14 is a rotor shaft 18 having mounted thereon in alternating disposition with the stationary blades 16 a predetermined number of annular arrays of rotating blades 20. The casing 14 confines and guides a flow of high pressure, high temperature motive fluid, commonly steam, over the alternating arrays of stationary blades 16 and rotating blades 20 to convert the high temperature and high pressure energy carried by the steam into rotational mechanical energy.

The flow of high pressure, high temperature motive fluid originates from a steam generator element 22 and is conducted through suitable conduits 24 into an inlet 26 disposed in the turbine casing 14. The steam, after expanding through the turbine 12, is exhausted through an exhaust conduit 28 and is conducted either to a condenser element (not shown) or to other lower pressure turbine elements (not shown). In addition to the inlet conduit 24, other piping means are interconnected with the casing 14, such as a hot reheat conduit 30, and extraction conduit 32, or gland steam piping 34, which supplies sealing steam to a set of gland seals 36 surrounding the rotor 18. Suitable flow control equipment, such as valving 40, are connected to and controlled by a turbine control system 42, which, in addition to controlling the rate of influent motive fluid into each turbine in the power plant 10, controls various other parameters of the system.

In the prior art, the induction of water into turbines has caused, in several instances, damage to the turbine element which necessitates costly down time and inactivity in order to make needed repairs. The water is produced due to a variety of reasons and may be introduced into the turbine through any of the conduits described above or through the other interconnected piping arrangements omitted from FIG. 1 for clarity. However, whatever the source and through whichever entry orifice introduced, the presence or induction of water into the turbine causes excessive damage thereto.

In order to attempt to ascertain whether water is present in any conduit leading into the turbine apparatus, the prior art has disposed thermocouple sensors either in the turbine casing itself or in any of the associated conduits leading thereinto. However, such provision of thermocouple sensors has been proven inadequate since the response time available after detection of water in the vapor flow is too short to initiate action to prevent damage to the turbine thereby.

In FIG. 1, reference numeral 50 indicates moisture being carried within a flow of motive fluid, the flow being indicated by reference arrow 52. The moisture may be generated from a variety of sources within the system, for example, moisture carry-over from the finishing desuper heater during a generator-load transient, or from moisture injected into the conduit from a desuper-heating spray system.

In order to indicate the presence of moisture in a vapor flow confined within any conduit leading into the turbine, apparatus 48 for indicating the presence of moisture is provided. Although the apparatus 48 is indicated as attached to the inlet conduit 24, it is to be understood that an apparatus 48 embodying the teachings of this invention may be disposed on any conduit or piping arrangement for which is felt necessary to ascertain whether moisture is being conducted in the vapor flow confined therein. The flow 52 of steam vapor from the steam generator 22 to the high pressure turbine for a fossil fuel plant is usually high pressure, high temperature superheated steam, having a pressure of between 1800 and 3500 pounds per square inch and 1000°F temperature, although it is to be understood that the apparatus 48 may also be advantageously used in a nuclear steam power plant where saturated steam is common.

The apparatus 48 comprises, as elements thereof, means 54 for detecting sonic energy modulations due to a moisture condition effect superimposed on background steam flow noise and means 56 for converting the sonic energy modulations so detected into an electrical signal. Noise suppression means 58 for eliminating extraneous signals carried within the generated electrical signal, for example, noise created by control electronic apparatus, are provided. Amplifying means 60 and envelope-detecting means 62 are connected between the output of the supression means 58 and comparator means 64. The comparator means 64 includes circuitry for comparing the voltage output of the envelope detector 62 with a reference signal. If, as will be explained herein, the detected signal from the means 62 differs from the reference signal by a predetermined magnitude, an actuation signal is generated by the comparator 64 and transmitted to the control system 42 through a control linkage 66.

In operation, the means 54 for detecting sonic energy comprises at least one turn of wire, or other sonic energy conductor, non-intrusively mounted around the conduit 24 and connected to a transducer element which comprises the energy conversion means 56. Usually the transducer is unable to withstand the hostile conditions generated by the high temperature and high pressure fluid confined within the conduit and for this reason, the standoff wire 54 is provided so as to acoustically link the conduit with the transducer while maintaining the transducer in any environmentally protected position.

In has been empirically determined that the moisture droplets 50, generated by any mechanism within the conduit 24, will randomly impinge upon the interior of the conduit within a very short distance from their source. This distance has been observed to be within 20 to 50 pipediameters of the source. If the standoff wire 54 is non-intrusively mounted on the exterior of the conduit 24 within a few pipediameters downstream of the moisture source, the acoustic energy generated by the impingement of the droplets on the interior of the conduit 24 is conducted by the acoustically-conductive material of the wire standoff 54 into the transducer element 56.

The acoustic signal conducted to the transducer 56 is converted from mechanical to electrical energy thereby, and the electrical signal is then passed through the noise suppression means 58, commonly a filter circuit. The filter circuit prevents extraneous signals caused by some unassociated electronic apparatus or induced by some unassociated mechanical vibration in the system from triggering the response hereinafter described. It has been found that the electrical frequency spectrum resulting from the conversion of sonic energy to an electrical signal occupies a broad band of frequencies. However, to insure that only electrical signals induced by the water-induced sonic energy are present, a band of electrical signals from the limits of 100 kilohertz to 1.0 megahertz is passed by the filter 58. The output of the filter 58 is amplified by the amplifier 60 and the envelope of the amplified signal is detected by the envelope detector 62. Any suitable circuit arrangement may be used to comprise the detector 62, FIG. 1 illustrating a rectifier 68 connected to a low pass filter 70, although other circuit configurations may be advantageously employed.

Experimentation has shown that the impingement of moisture droplets on the interior of the conduit 24 close to the source of the moisture results in an increase in the magnitude detected by the standoff 54 over the normal steam "flow noise" detected and associated with the normal passage of the fluid within the conduit. That is, when water droplets impinge upon the interior of the conduit 24 at a point close to the source of the moisture, the magnitude of the mechanical (and electrical) signal exceeds the normal background magnitude which is detected when only pure steam passes therethrough.

As seen by inspection of FIG. 1, this situation is depicted by waveform 72, which illustrates the output voltage of the amplifier 60 as a function of time for a standoff 54 that is located relatively close to a moisture source. In the waveform 72, for the time period $0<t<t_1$, the output of the amplifier 60 is shown as electrical voltages corresponding to the background noise associated with a flow of pure steam within the conduit 24. However, at and after time $t_1$, when the noise created by the introduction of water from a source relatively close to the standoff 54 is detected by the standoff 54, the electrical voltage output of the amplifier 60 increases in amplitude over the amplitude of the signal associated with the pure steam noise.

The output of the amplifier 60 passes through the envelope detector 62, where the signal is rectified and filtered. As seen by waveform 74, the rise in output voltage due to the introduction of moisture into the steam flow is clearly visible. The detector 62 output is fed to the comparator 64 where the detector signal 74 is compared to a reference signal. Circuitry is provided within the comparator 64 which obtains the difference between the detector signal 74 and the reference signal and which emits an actuating signal, shown as a pulse 76 in waveform 78, to the control system 42 if the detector signal 74 differs from the reference signal by a predetermined magnitude. In the case here discussed, for a standoff 54 located close to the water source, if the detector signal 74 is determined to exceed the reference signal by at least the predetermined magnitude, the pulse 82 is emitted.

Empirical studies have also shown that the farther downstream one proceeds from the source of the moisture 50, a phenomenon known as a "quieting effect" occurs. Physically, the situation close to the moisture source shows the moisture droplets impinging against the interior of the conduit within a very few pipediameters from the source. The moisture then "plates" on the interior of the conduit, and a thin film of water is then swept along the interior of the conduit by the steam flow.

As a consequence of the "plating" of moisture droplets on the interior of the conduit, if the wire standoff 54 were to be non-intrusively mounted on the exterior of the conduit at a location far downstream of the moisture source, the magnitude the signal detected will be less than the background signal. The diminution in detected signal far downstream in attributable to at least three factors: 1) Ultrasonic damping caused by a film of water on a relatively thin conductor (i.e., the conduit) of ultrasonic energy; 2) decrease in flow noise produced at the steam/conduit interface due to the change in the "roughness" factor that a streaming water film within a conduit produces; and 3) the streaming water film producing an isolation layer to soften the impact of any residual water droplets and/or to decrease the coupling of steam flow noise to the conduit wall.

This alternative situation, where the standoff 54 is located far downstream from the source of moisture, is illustrated by the waveform 80, where the output voltage of the amplifier 60 as a function of time is depicted. As with 72 waveform described above for the standoff location near the moisture source, the waveform 80 shows that for a time period $0<t<t_1$, there occurs electrical signals of a magnitude corresponding to the background noise associated with the flow of pure steam within the conduit 24. But, for time after $t_1$, when the noise created by the moisture and moderated by the quieting effect, is detected by the standoff 54, the electrical voltage output of the amplifier 60 decreases in amplitude relative to the amplitude of the signal associated with the pure steam noise.

The output of the amplifier 60 is passed through the envelope detector 62 and the resultant envelope is depicted in waveform 82. Here the dramatic decrease in signal amplitude due to the quieting effect is clearly shown. The detector output passes to the comparator 64 where the detector signal 82 is compared to a reference signal. As stated above, the comparator 64 contains circuitry which obtains the difference between the detector signal 82 and the reference signal and which emits an actuating signal, shown again as a pulse 84 in waveform 86, to the control system 42 if the detector signal 74 differs from the reference signal by a predetermined magnitude. In this instance, for a standoff location far from the moisture source, if the detector signal 82 is determined to be less than the reference signal by at least the predetermined magnitude, the pulse 84 is emitted.

Experimental results have indicated that the predetermined reference signal level may be adjusted so that small scale random perterbations of the detector signals are not sufficient to trigger the alarm pulse. However, it is noted that setting the reference signal at such a level does not significantly diminish the sensitivity of the device 48 in indicating the presence of moisture in the steam flow.

It should also be understood that the reference signal may be either a fixed D.C. voltage or may vary as a function of the voltage levels generated by the immediately prior steam flow noise. This variable, or "floating," reference level is advantageous in eliminating false alarm signals under gradually changing steam flow noise characteristics.

To recapitulate: In general, the source point of moisture within the conduit 24 is an unknown, the only controllable parameter being the external location on the conduit at which the standoff wire 54 is non-intrusively attached. If the point of non-intrusive contact is relatively close to the point of moisture source, an increase in the signal detected over a background reference signal is obtained. Alternatively, if the point of non-intrusive contact is far downstream of the point of moisture source, a decrease in detected signal below the background reference is obtained. Thus, the comparator means 60 is provided with circuitry to compare the detected electrical signal with the background reference and to generate an indicator signal if the detected signal is either above or below the background signal by a predetermined amount.

In regard to the initial location of the standoff 54, it is understood that it may be placed at any convenient location on the conduit. However, if there is expected to be a laminar flow pattern within the conduit at the point at which the measurements are taken, the standoff 54 is most advantageously disposed at a bend in the piping. However, if a pure turbulent flow pattern is expected, random impingement of moisture droplets, if present, will be encountered at any position within the conduit, even along a relatively long, straight run.

It is to be emphasized that the presence of moisture in a steam conduit is an anomalous condition, and, for this reason, the first indication of the presence of moisture, as detected by the apparatus 48, should lead to an interruption of the flow by the turbine control 42. However, it, for some reason a "false alarm" should occur, and the flow to the turbine 12 be interrupted, possible serious consequences, in addition to high costs attendant upon reintroducing fluid flow to the turbine, are encountered. As an example of phenomenon causing a possible false alarm, if superheated steam is utilized in the power plant 10, the introduction of water into the superheated steam flow would quickly begin to flash into steam. Yet, if the standoff 54 in, by happenstance, located at the point of water introduction, an alarm signal is generated, even though in a short period of time that water will flash into harmless steam. It is for this reason—to reduce the probability of steam flow interruptions when no moisture is present—i.e., a false alarm—that the embodiment of the invention shown in FIG. 2 is utilized.

Figure 2:
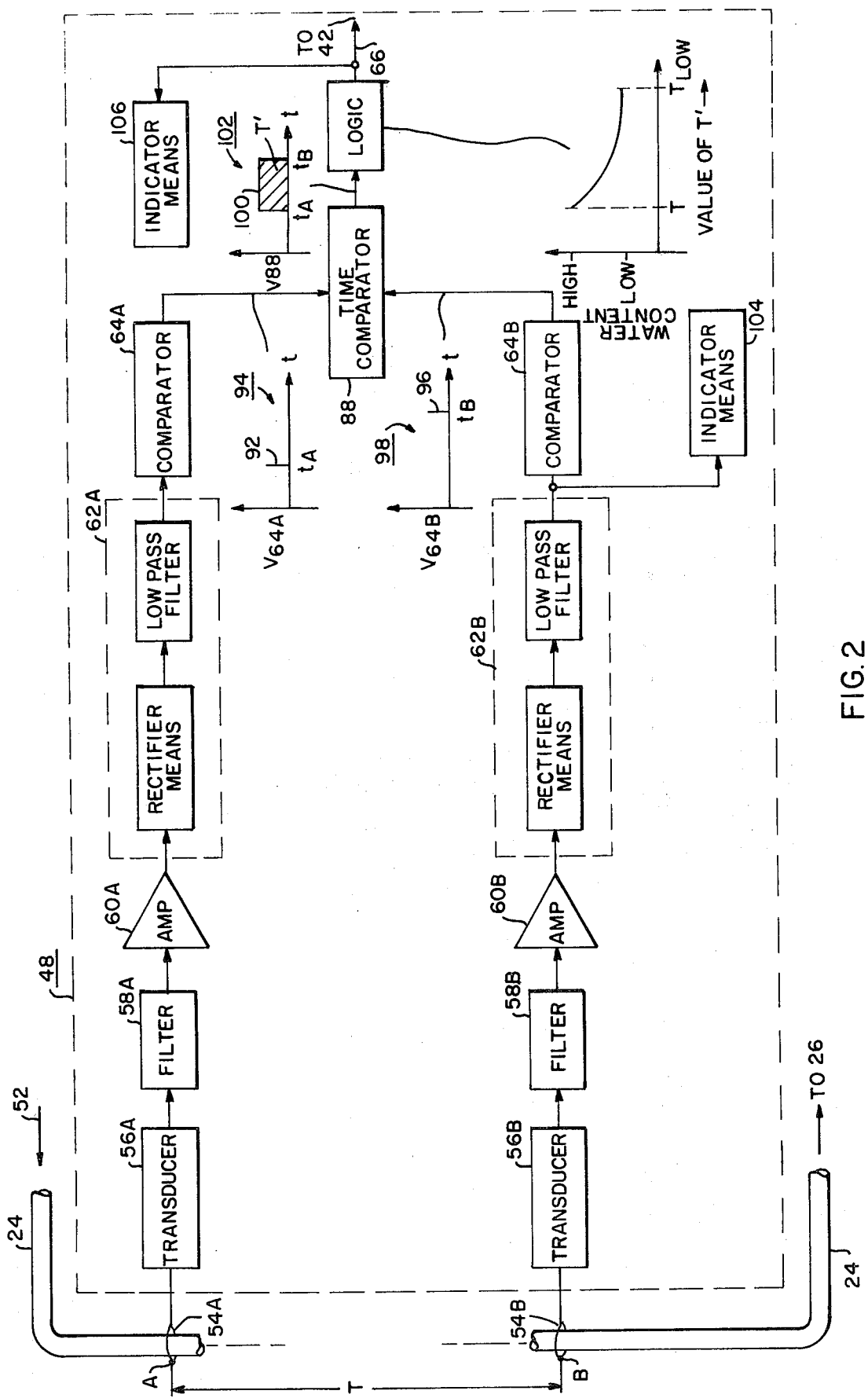
FIG. 2 is a diagrammatic view of an alternative embodiment of an apparatus for indicating the presence and amount of moisture in a fluid flow confined within a conduit embodying the teachings of this invention.

Referring now to FIG. 2, a diagrammatic view of an alternative embodiment of the moisture detention apparatus 48 is shown. In FIG. 2, the vapor flow 52 has a predetermined flow rate, $r$, associated therewith. The apparatus 48 in FIG. 2 comprises a detector means 54A and 54B located respectively at a first point A and a second point B on the conduit 24. Points A and B are separated by a predetermined distance on the conduit 24 which, for a particular flow rate, $r$, and a particular conduit size, among other parameters, a steam particle carried within the vapor flow 52 can be expected to pass point B a predetermined time period T after it has passed point A.

It is to be understood that this time differential T is the time it would take a steam particle to move between points A and B and this time becomes useful as a reference standard as will be explained herein.

In the embodiment shown in FIG. 2, the detector means 54A and 54B comprises a first standoff wire sensor and a second standoff wire sensor each connected to an associated transducer 56A and 56B. The standoffs 54A and 54B are fabricated of material similar to that used in FIG. 1. Associated with each transducer 56A and 56B is a filter element 58A and 58B and amplifiers 60A and 60B, respectively. Envelope detectors 62A and 62B, each having a rectifier and low pass filter, is connected between the outlets of the amplifiers 60A and 60B and comparator elements 64A and 64B. As seen, the device shown in FIG. 2 basically comprises a device as taught in FIG. 1 disposed at points A and B on the conduit 24. However, due to the manner in which the outputs of these separate devices are utilized together, as will be described herein, the device shown in FIG. 2 significantly reduces the problem of false alarms and provides accurate, reliable indication of the presence of water in the steam flow.

The outputs of both of the comparators 64A and 64B are connected to a time comparator 88, the output of which is in turn connected to a logic element 90. The output of the logic 90 is linked, through a control linkage 66A, to the turbine control system 42.

In operation, similar to the operation of the device of FIG. 1, whenever there is moisture present in the conduit 24, from whatever the source, the sonic energy thereof is detected by the standoff 54A. Depending on the location of the standoff 54A relative to the source of the moisture, the magnitude of the energy detected is either greater than or less than a predetermined reference signal. As explained in conjunction with FIG. 1, if the positive or negative differential between the detector signal and the reference signal exceeds a predetermined magnitude, the comparator 64A emits a pulse 92 occurring at a time $t_A$, corresponding to the time at which the sonic energy of the moisture is detected at point A, as shown on waveform 94.

Similarly, at point B, if moisture is present in the steam flow 52, a period of time elapses until that moisture is carried to point B where the standoff 54B detects the sonic energy associated with the entrained moisture. Similar to the operation outlined in connection with FIG. 1, the output of the comparator 64B emits, at time $t_B$, a pulse 96 indicating that moisture is present at point B, as seen in waveform 98. Of course, since the standoff 54B is located, by definition, a far distance on the conduit 24 from point A, the quieting effect, as discussed above, is in full play as the moisture passes point B. Therefore, the pulse 96 is emitted by the comparator 64B if the detector signal 62B is less than the reference signal by the predetermined. In any event, however, the output of the comparator 64A—the pulse 92 occurring at time $t_A$—and the output of the comparator 64B—the pulse occurring at time $t_B$—are both introduced into the time comparator 88.

The purpose of the time comparator 88 is to ascertain the difference in time between the input pulses $t_A$ and $t_B$. The time comparator 88 contains electrical circuitry which emits a pulse 100, as seen on waveform 102, which extends in duration for a period of time equal to $(t_B - t_A)$. For example, the time comparator may contain circuitry which is activated by the pulse 92 from the comparator 64A and which is deactivated by the pulse 96 from the comparator 64B. The comparator 88 is thus turned "on", and begins pulse 100, at a time $t_A$ upon receipt of the pulse 92, and is turned "off," stopping pulse 100, at a time $t_B$ on receipt of the pulse 96. Of course, this is merely illustrative of one possible circuit arrangement for the time comparator 88 which results in the pulse 100 durating for the period of time $(t_B - t_A)$. From the time comparator 88, the pulse 100 is fed to the logic element 90. For ease of discussion, hereafter the pulse 100 from the time comparator 88 is defined as having a duration $T^1$, it being understood that time $T^1$ is equal to the time period defined by $(t_B - t_A)$.

As mentioned earlier, a particle of steam carried within a flow of pure steam within a given conduit 24 at a given flow $r$ requires T seconds to move from point A to point B. It has also been empirically shown that the travel time of moisture entrained within a steam flow is affected by the amount of water therein. As seen within the logic 90 of FIG. 2, steam having a relatively high water content moves from point A to point B in a time very close to T seconds. As the water content decreases to lower values the flow time decreases, with a relatively low concentration of water requiring a period of $T_{low}$ seconds to move from point A to point B. Utilizing this empirically demonstrated fact, the logic 90 determines if the time $T^1$—the time duration of the pulse 100 indicating the detection of water at points A and B—is within a predetermined range of time values, for example, between T and $T_{low}$ seconds, a signal pulse is generated to the turbine control system 42.

This is, if the logic 90 determines that if the pulse $T^1$ has a time duration lying between time values T and $T_{low}$, the steam flow carries water of a sufficient amount to damage the turbine. Therefore, an alarm pulse is emitted to the turbine control to actuate control valving 40 and interdict the flow.

However, if the logic 90 determines that $T^1$ is of a greater duration than $T_{low}$, the water content of the steam is not sufficient to damage the turbine. It is to be understood, of course, that the precise value of $T_{low}$ is determined from the parameters of the particular power generation system with which the device 48 is used. In addition to the alarm to the turbine control 42, there may be added a secondary alarm indicator actuated by another pulse from the logic 90 if $T^1$ does extend for a duration longer than $T_{low}$. Such a secondary alarm can convey information to the effect that although there is water present in the steam flow it is of insufficient size to cause damage to the rotating elements of the plant.

For completeness, if $T^1$ is determined to be of a lesser duration than T seconds, such a detected signal may properly be disregarded. This situation indicates that some sonic disturbance, for example dropping of a wrench onto the conduit 24, has been set up which travels in the conduit 14 faster than the steam flow 52. The ability of the device 48 shown in FIG. 2 to disregard such mechanical disturbances is a further example of the increased immunity to false alarms of any sort exhibited by the device embodying the teachings of this invention.

It may be appreciated that the apparatus shown in FIG. 2 provides a more highly reliable and discriminating arrangement for detecting the presence of moisture in the steam flow; and therefore significantly reduces the probability of a false alarm signal being generated.

In addition to detecting the presence of moisture in the steam flow, the device shown in FIG. 2 also provides an indication of the relative amount of moisture present in both saturated and superheated steam. In the case of a saturated steam flow, this indication of relative amount of moisture present may be calibrated to produce a steam quality indicator.

There are two independent methods available to ascertain the relative amount of moisture in the steam flow, both of which are adaptable for use in the apparatus shown in FIG. 2.

The first method of indicating relative amount of moisture utilizes the empirically shown relationship between the moisture amount and the magnitude of the change of sonic signal detected within the conduit. It has been observed that there is a monotonically functional equivalence between the magnitude of signal change and the relative amount of moisture present.

The largest signal change has been shown to occur where large, damaging "slugs" of water are present in the system. Thus, in addition to merely detecting the presence of water, the magnitude of the change of signal level relative to the reference signal reveals much as to the relative amount of moisture present. Large slugs of water have a greater effect on the change between detected entrained in the steam flow is a damaging water condition. However, if the time interval $T^1$ is not within the range of values sufficient to trigger the alarm signal, the relative amount of moisture present is not dangerous. This time difference may be calibrated on a suitable indicator 106 connected most advantageously within the device of FIG. 2 at the output of the logic circuitry 90.

To recapitulate: The apparatus 48 shown in FIG. 2 may be used to indicate the relative amount of moisture present in the steam flow in addition to indicating the presence of moisture therein in two ways. If the time interval between the detection of sonic energy at points A and B is calibrated on a suitable device, the relative amount of moisture present may be indicated. Another method utilizes the observed fact that the magnitude of change in sonic signal is functionally related to the relative amount of moisture present. This change may also be independently calibrated and displayed. Of course, although both methods are independently available, they may be combined to produce a single, reliable, and accurate indicator as to the relative amount of moisture present in the steam flow. Such a capability is over and above the ability of the device shown in FIG. 2 to detect accurately and reliably the presence of moisture in the system.

In overall summary, then, it is thus appreciated that apparatus embodying the teachings of this invention provide indications as to the presence and relative amount of moisture within a vapor flow in a reliable manner. The non-intrusive mounting of this device maintains the integrity of the vapor carrying conduit, yet permits accurate indications of potentially damaging moisture presence in time to initiate prophylactic measures.

We claim as our invention:

1. A steam turbine comprising:
    a casing having rotating and stationary blades therein,
    conduit means for conducting an elastic fluid vapor into and out of said casing and,
    first means for detecting sonic energy produced within the conduit by the moisture, the first means being mounted on said conduit at a first predetermined location,
    second means for detecting sonic energy variations produced within the conduit by the moisture, said second means being mounted on said conduit at a predetermined location spaced a predetermined distance from said first predetermined location,
    means for converting the sonic energy detected by said first and said second detecting means into a first and a second electrical signal,
    means for comparing the magnitude of each of said electrical signals with a predetermined magnitude and for generating a signal indicating that both electrical signals differ in magnitude from said predetermined magnitude,
    means for determining the time difference between said first and said second electrical signals, and for comparing said time difference with a predetermined time value, and for generating a signal indicating the time difference between said first and said second electrical signals substantially equal said predetermined time value, and means responsive to said signals generated by said magnitude-comparing means and said time-comparing means for indicating the presence and amount of moisture droplets within said vapor flow.

2. The apparatus of claim 1 wherein:
said first and said second detector means are non-intrusively mounted external to said conduit,
wherein said predetermined time value is functionally dependent upon the amount of time a fluid particle would require to travel from the first to the second predetermined location within said conduit if carried by a vapor flow moving at a predetermined flow rate therewithin
and wherein said apparatus further comprises means for suppressing noise carried by said first and said second electrical signals.

3. The apparatus of claim 1, wherein said magnitude-comparing means generates said signal if the magnitude of the first and the second electrical signal is greater than the predetermined magnitude.

4. The apparatus of claim 1, wherein said magnitude-comparing means generates said signal if the magnitude of the first and the second electrical signal is less than the predetermined magnitude.

* * * * *